US009115062B2

(12) United States Patent
Hierse et al.

(10) Patent No.: US 9,115,062 B2
(45) Date of Patent: Aug. 25, 2015

(54) FLUOROSURFACTANTS

(75) Inventors: Wolfgang Hierse, Gross-Zimmern (DE); Eckhard Claus, Frankfurt am Main (DE); Jan Krause, Nidda-Eichelsdorf (DE); Melanie Kleineidam, Darmstadt (DE); Steffen Schellenberger, Darmstadt (DE); Andreas Bathe, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 809 days.

(21) Appl. No.: 13/379,438

(22) PCT Filed: Jun. 1, 2010

(86) PCT No.: PCT/EP2010/003328
§ 371 (c)(1),
(2), (4) Date: Dec. 20, 2011

(87) PCT Pub. No.: WO2010/149242
PCT Pub. Date: Dec. 29, 2010

(65) Prior Publication Data
US 2012/0111233 A1   May 10, 2012

(30) Foreign Application Priority Data

Jun. 26, 2009   (DE) .................. 10 2009 030 846

(51) Int. Cl.
| | | |
|---|---|---|
| *C07C 309/17* | (2006.01) | |
| *C08K 5/42* | (2006.01) | |
| *B01F 17/00* | (2006.01) | |
| *C07C 67/08* | (2006.01) | |
| *C07C 69/65* | (2006.01) | |
| *C07C 303/06* | (2006.01) | |
| *C08F 2/24* | (2006.01) | |
| *C09D 5/02* | (2006.01) | |
| *C09D 7/06* | (2006.01) | |
| *C09D 7/12* | (2006.01) | |
| *C09D 11/03* | (2014.01) | |
| *C11D 1/00* | (2006.01) | |
| *D06M 13/236* | (2006.01) | |
| *D06M 13/256* | (2006.01) | |
| *C08K 5/103* | (2006.01) | |

(52) U.S. Cl.
CPC ........... *C07C 309/17* (2013.01); *B01F 17/0035* (2013.01); *C07C 67/08* (2013.01); *C07C 69/65* (2013.01); *C07C 303/06* (2013.01); *C08F 2/24* (2013.01); *C09D 5/027* (2013.01); *C09D 7/06* (2013.01); *C09D 7/1233* (2013.01); *C09D 11/03* (2013.01); *C11D 1/004* (2013.01); *D06M 13/236* (2013.01); *D06M 13/256* (2013.01); *C08K 5/103* (2013.01); *D06M 2200/11* (2013.01); *D06M 2200/12* (2013.01)

(58) Field of Classification Search
None
See application file for complete search history.

(56) References Cited

U.S. PATENT DOCUMENTS

| | | | |
|---|---|---|---|
| 2,619,500 | A | 11/1952 | Chiddix et al. |
| 4,988,610 | A | 1/1991 | Pitt et al. |
| 5,157,159 | A | 10/1992 | Janulis et al. |
| 5,300,394 | A | 4/1994 | Miller et al. |
| 6,890,608 | B2 | 5/2005 | Morishima et al. |
| 8,008,358 | B2 | 8/2011 | Kirsch et al. |
| 2008/0149878 | A1 | 6/2008 | Kirsch et al. |

FOREIGN PATENT DOCUMENTS

| | | |
|---|---|---|
| DE | 10 2005 000 858 A1 | 7/2006 |
| JP | 6-214334 A | 8/1994 |
| JP | 8-134371 A | 5/1996 |
| JP | 9-111286 A | 4/1997 |
| JP | 2001-133984 A | 5/2001 |
| WO | 03/010128 A2 | 2/2003 |

OTHER PUBLICATIONS

Kennedy, G.L., et al., "The Toxicology of Perfluorooctanoate," Critical Reviews in Toxicology, 2004, 34(4), pp. 351-384, Taylor and Francis Inc.
Pitt, A.R., et al., "The relationship between surfactant structure and limiting values of surface tension, in aqueous gelatin solution, with particular regard to multilayer coating," Colloids and Surfaces A: Physicochemical and Engineering Aspects 114, Feb. 15, 1996, pp. 321-335; Elsevier Science B.V.
Pitt, A.R., "The efficiency of dynamic surface tension reductions within homologous series of surfactants in aqueous gelatin solution," Program Colloid Polym Sci, 1997, 103, pp. 307-317.
Liu, Z., et al., "Phase Behaviours of Aerosol-OT Analogue Fluorinated Surfactants in 1,1,1,2-Tetrafluoroethane and Supercritical CO2," Industrial and Engineering Chemistry Research, 2007, 46 (1), pp. 22-28.
Heilmann, S.M., et al., "O-Hydroxyethylation of 1,1-dihydroperfluorinated alcohols," Journal of Fluorine Chemistry, 1992, 59, p. 387-396, Elsevier Sequoia.
Carlson, D.P. et al., "Fluoropolymers, Organic," Ullmann's Encyclopedia of Industrial Chemistry, 2005, retrieved from the internet: http://onlinelibrary.wiley.com/doi/10.1002/14356007.all, pp. 1-40; Cited in International Search Report, dated Oct. 26, 2010, issued in corresponding PCT/EP2010/003328.
International Search Report, dated Oct. 26, 2010, issued in corresponding PCT/EP2010/003328.

(Continued)

*Primary Examiner* — Kamal Saeed
(74) *Attorney, Agent, or Firm* — Millen, White, Zelano & Branigan, P.C.

(57) ABSTRACT

The present invention relates to novel compounds containing fluorinated end groups, to the use thereof as surface-active substances, and to processes for the preparation of these compounds.

26 Claims, 1 Drawing Sheet

(56) References Cited

OTHER PUBLICATIONS

English Translation of Japanese Office Action dated May 13, 2014 issued in corresponding Japanese Patent Application No. 2012-516543 (pp. 1-5).

S. Gold et al., "Branched Trichain Sulfosuccinates as Novel Water in $CO_2$ Dispersants", Colloid Polymer Science, vol. 284 (2006) pp. 1333-1337.

English Translation Abstract of JP 6-214334 published Aug. 5, 1994.

English Translation Abstract of JP 8-134371 published May 28, 1996.

Figure 1:
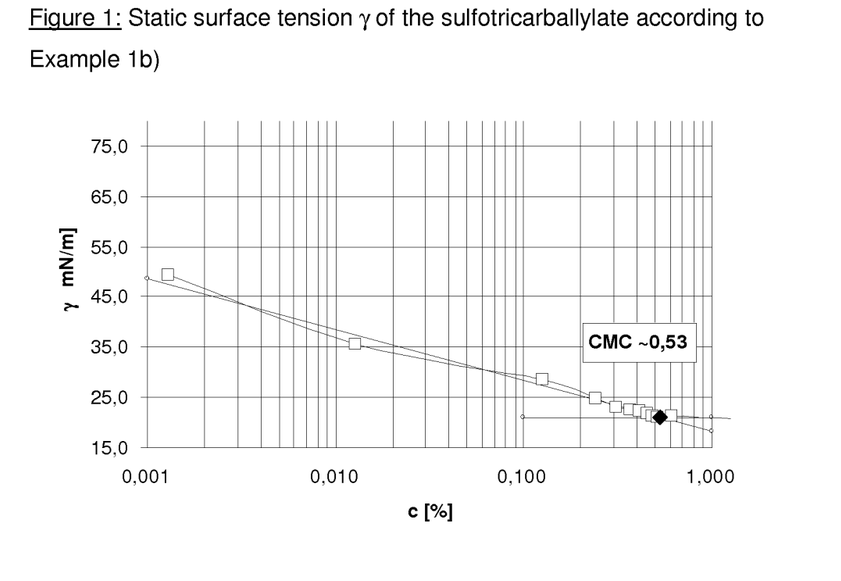

Figure 1: Static surface tension γ of the sulfotricarballylate according to Example 1b)

Figure 2:
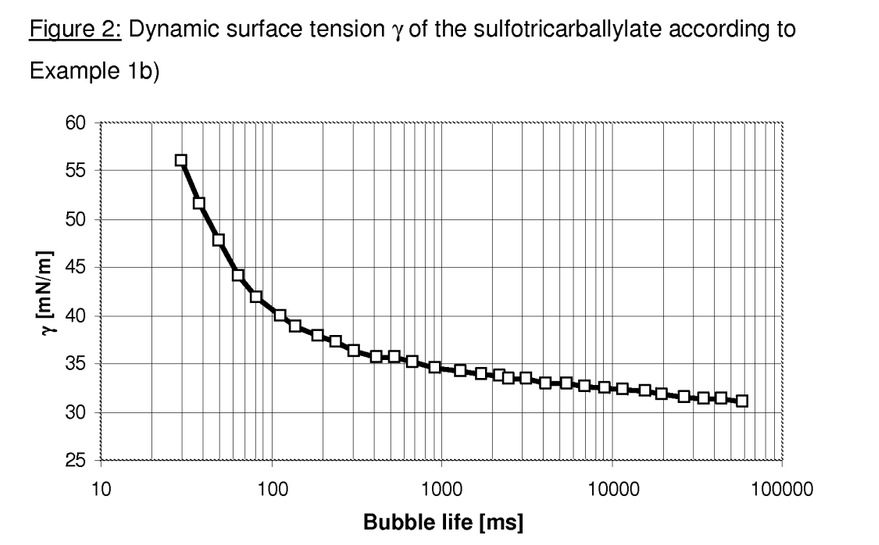

Figure 2: Dynamic surface tension γ of the sulfotricarballylate according to Example 1b)

FLUOROSURFACTANTS

The present invention relates to novel compounds containing fluorinated end groups, to the use thereof as surface-active substances, and to processes for the preparation of these compounds.

Fluorosurfactants have an outstanding ability to reduce surface tension, which is utilised, for example, in the hydrophobicisation of surfaces, for example of textiles, paper, glass, building materials or adsorbents. In addition, it is possible to use them as interface promoter or emulsifier or viscosity reducer in paints, surface coatings or adhesives.

In general, fluorosurfactants contain perfluoroalkyl substituents, which are broken down to perfluoroalkylcarboxylic acids (PFCAs) and -sulfonic acids (PFASs) in the environment by biological and/or other oxidation processes. In recent years, the accumulation of perfluoroalkylcarboxylic acids (PFCAs) and perfluoroalkylsulfonic acids (PFASs) in nature has given cause for concern. PFCAs and PFASs are highly persistent compounds whose long-chain variants (containing perfluoroalkyl chains of 8 or more carbon atoms) have a bioaccumulative potential. They are in some cases suspected of causing health problems (G. L. Kennedy, Jr., J. L. Butenhoff, G. W. Olsen, J. C. O'Connor, A. M. Seacat, R. G. Biegel, S. R. Murphy, D. G. Farrar, Critical Review in Toxicology, 2004, 34, 351-384).

Specific applications of sulfotricarballylates containing optionally fluorinated alkyl groups or aryl groups are described in U.S. Pat. No. 4,988,610, U.S. Pat. No. 6,890,608 and in A. R. Pitt et al., Colloids and Surfaces A: Physicochemical and Engineering Aspects, 1996, 114, 321-335; A. R. Pitt, Progr. Colloid Polym. Sci., 1997, 103, 307-317 and Z.-T. Liu et al., Ind. Eng. Chem. Res. 2007, 46, 22-28.

The Omnova company markets polymers whose side chains contain terminal $CF_3$ or $C_2F_5$ groups. International Patent Application WO 03/010128 describes perfluoroalkyl-substituted amines, acids, amino acids and thioether acids which contain a C3-20-perfluoroalkyl group.

JP-A-2001/133984 discloses surface-active compounds containing perfluoroalkoxy chains which are suitable for use in antireflection coatings. JP-A-09/111,286 discloses the use of perfluoropolyether surfactants in emulsions. DE 102005000858 A1 describes compounds which carry at least one terminal pentafluorosulfuranyl group or at least one terminal trifluoromethoxy group and contain a polar end group, are surface-active and are suitable as surfactants.

There continues to be a demand for alternative surface-active substances, preferably having a property profile comparable to that of classical fluorosurfactants and equally great chemical versatility, which are preferably not degraded to long-chain persistent fluorocarboxylic or fluorosulfonic acids on oxidative or reductive degradation or are preferably effective as conventional fluorosurfactants in relatively low dosage.

Novel compounds have now been found which are suitable as surface-active substances and preferably do not have one or more of the above-mentioned disadvantages.

The present invention relates firstly to compounds of the formula (I)

where
the groups $Z_i$ ($Z_1$, $Z_2$ and $Z_3$) are, independently of one another, branched or unbranched alkyl groups or groups of the structure $R_f(A(CR^1R^2)_{ci}\text{—}(CR^3R^4)_{c'i})_{di}\text{—}$, where the respective indices ci and c'i are, independently of one another, 0-10, and di=0-5, where $R_f$ is a branched or unbranched, fluorine-containing alkyl radical, $R^1$ to $R^4$ are, independently of one another, hydrogen or a branched or unbranched alkyl group, ci and c'i are not simultaneously 0, and A=O, S and/or N,
$Y_1$ is an anionic polar group and $Y_2$ is a hydrogen atom, or vice versa,
X is a cation,
and at least one of the groups $Z_i$ is a group of the structure $R_f(A(CR^1R^2)_{ci}\text{—}(CR^3R^4)_{c'i})_{di}\text{—}$.

It is preferred for formula (I) that a) di>0 if $Z_1$, $Z_2$ and $Z_3$ are all a group of the structure $R_f(O(CH_2)_{ci})_{di}$ and all $R_f$ are selected from $CF_3CF_2CH_2$—, $CF_3CF_2CH_2CH_2$—, $CF_3CF_2CF_2CH_2$— or $H(CF_2)_4CH_2$— and/or that b) $Y_2$ is not equal to $OSO_3^-$ and X is not equal to $Na^+$ or $K^+$ if $Z_1=Z_2=Z_3$ and all $Z_i$ are selected from $C_4F_9CH_2CH_2$—, $C_6F_{13}CH_2CH_2$— or $C_8F_{17}CH_2CH_2$—.

The radicals $R_f$ are branched or unbranched, fluorine-containing alkyl groups. The radicals $R_f$ may be partly or perfluorinated and preferably contain terminal perfluorinated groups. Preference is given to branched or unbranched, fluorine-containing alkyl groups having 1 to 10 C atoms. Unbranched fluorine-containing alkyl groups preferably contain 1 to 6 C atoms, in particular 1-4 C atoms. Branched fluorine-containing alkyl groups preferably contain 3 to 6 C atoms, in particular 3-4 C atoms. The branched fluorine-containing alkyl groups used are preferably $(CF_3)_2$—CH— or $(CF_3)_3$—C— groups.

$R^1$ to $R^4$ are preferably, independently of one another, hydrogen or a $C_{1-4}$-alkyl group, in particular H or $CH_3$. ci and c'i are preferably, independently of one another, an integer from the range 0 to 6, in particular 0-3, particularly preferably 0-2, where ci and c'i are not simultaneously 0. di is preferably an integer from the range 0 to 3, particularly preferably 1-3, in particular 1.

A is preferably equal to O or S, in particular O. In particular, the groups $Z_i$ are equal to $R_f(O(CR^1R^2)_{ci}(CR^3R^4)_{c'i})_{di}$—.

Particular preference is given to compounds where $R^1$ to $R^3$ are equal to hydrogen, $R^4$ is equal to hydrogen or methyl, ci and c'i are, independently of one another, equal to 0-2, in particular 1, di is equal to 0-3, in particular 1-3, and A is equal to 0, where ci and c'i are not simultaneously 0. In a preferred variant of the invention, $R^4$ here is equal to methyl and the variables have these preferred meanings. Also suitable are compounds in which $R^1$ is equal to methyl and $R^2$ to $R^4$ are equal to hydrogen, where the variables have the preferred meanings.

Particular preference is given to compounds of the formula (I) in which the fluorine-containing groups $Z_i$ are equal to $R_f(O(CH_2)_{ci})_{di}$—, where the respective indices ci=2-10, preferably 2-4, in particular 2, and di=0-5, preferably 0-3, particularly preferably 1-3, in particular 1, $Y_1$ is an anionic polar group, and $Y_2$ is a hydrogen atom, or vice versa, X is a cation, and at least one of the groups $Z_i$ is a group of the structure $R_f(O(CH_2)_{ci})_{di}$—, where preferably a) d>0 if $Z_1$, $Z_2$ and $Z_3$ are all a group of the structure $R_f(O(CH_2)_{ci})_{di}$— and all $R_f$ are selected from $CF_3CF_2CH_2$—, $CF_3CF_2CH_2CH_2$—, $CF_3CF_2CF_2CH_2$— or $H(CF_2)_4CH_2$—, and b) $Y_2$ is not equal to $OSO_3^-$ and X is not equal to $Na^+$ or $K^+$ if $Z_1=Z_2=Z_3$ and all $Z_i$ are selected from $C_4F_9CH_2CH_2$—, $C_6F_{13}CH_2CH_2$— or $C_8F_{17}CH_2CH_2$—.

Preference is furthermore given to compounds of the formula (I) in which $Z_1$, $Z_2$ and $Z_3$ are, independently of one another, $F_3C(CF_2)_{ai}(CH_2)_{bi}$—$(O(CH_2)_{ci})_{di}$— groups, where ai=0-6, preferably 1-5, in particular 1-2, bi=1-6, preferably 1-3, in particular 1-2, ci=2-10, preferably 2-4, in particular 2, and di=0-5, preferably 1-3, in particular 1, where, in particular, $Z_1=Z_2=Z_3$. Preference is also given to compounds in which ai=0, 1 or 2, preferably 1 to 2, in particular 1, bi=1, ci=2, and di=1 or 2, in particular 1, and where $a_1+a_2+a_3>1$.

If all $Z_1$, $Z_2$ and $Z_3$ are selected from $CF_3CF_2CH_2$—, $CF_3CF_2CH_2CH_2$—, $CF_3CF_2CF_2CH_2$— or $H(CF_2)_4CH_2$—, di in formula (I) is preferably greater than 0. If $Z_1=Z_2=Z_3$ and all $Z_i$ are selected from $C_4F_9CH_2CH_2$—, $C_6F_{13}CH_2CH_2$— or $C_8F_{17}CH_2CH_2$—, $Y_2$ is not equal to $OSO_3^-$, and X is not equal to $Na^+$ or $K^+$.

In an embodiment of the invention, the compounds according to the invention can be in the form of mixtures, in which the individual compounds have different values for ci, c'i and/or di.

The compounds of the formula (I) according to the invention may contain one or more fluorinated groups $Z_i$ according to the invention. The compounds preferably contain two or three fluorinated groups $Z_i$, particular preference being given to those containing three fluorinated groups $Z_i$.

The three substituents $Z_1$, $Z_2$ and $Z_3$ may all be identical, may all be different or two of them may be identical and one of them different, with the proviso that $Z_1$, $Z_2$ and $Z_3$ are not all simultaneously unfluorinated, branched or unbranched alkyl radicals. Preferred compounds are those in which two of $Z_1$, $Z_2$ and $Z_3$ or all of $Z_1$, $Z_2$ and $Z_3$ are identical, in particular equal to the preferred $R_f(O(CR^1R^2)_{ci}(CR^3R^4)_{c'i})_{di}$— groups described. Very particular preference is given here to the following fluorine-containing alkyl radicals: $CF_3CH_2$—, $CF_3CF_2CH_2$—, $CF_3CF_2CF_2CH_2$—, $CF_3CF_2CH_2CH_2$—, $CF_3CF_2CH_2CH_2CH_2$—, $CF_3CFHCF_2CH_2$—, $(CF_3)_2CH$—, $(CF_3)_3C$—, $CF_3(CF_2)_3$—$CH_2CH_2$—, $CF_3(CF_2)_5CH_2CH_2$—, $CF_3(CF_2)_4CH_2$—. The compounds preferably include fluorine-containing alkyl radicals having at most 3 fluorine-carrying carbon atoms. Particularly preferred compounds of the formula (I) where $Z_1=Z_2=Z_3$ are those in which ci or c'i is equal to 0 to 3, in particular 0-2, and di>0, where ci and c'i are not simultaneously 0. Compounds according to the invention where di is equal to 1 to 3, in particular 1, are especially preferred.

If the compounds contain unfluorinated end groups $Z_1$, $Z_2$ and $Z_3$, these are preferably, independently of one another, linear or branched alkyl having 1 to 20 C atoms, preferably 1 to 10 C atoms. In particular, $Z_1$, $Z_2$ and $Z_3$ are, independently of one another, linear alkyl having 3 to 10 C atoms, particularly preferably having 3 to 8 C atoms. If two of the groups $Z_1$, $Z_2$ and $Z_3$ are unfluorinated, these two groups are preferably identical.

In a preferred group of compounds to be employed in accordance with the invention or compounds according to the invention, $Y_1$ and $Y_2$, where one of the two is equal to a hydrogen atom, stand for an anionic polar group selected from —$COO_3^-$, —$SO_3^-$, —$OSO_3^-$, —$OPO_3^{2-}$, —$(OCH_2CH_2)_s$—O—$(CH_2)_t COO^-$, —$(OCH_2CH_2)_s$—O—$(CH_2)_t SO_3^-$, —$(OCH_2CH_2)_s$—O—$(CH_2)_t OSO_3^-$, —$(OCH_2CH_2)_s$—O—$(CH_2)_t$—$PO_3^{2-}$—, —$(OCH_2CH_2)_s$—O—$(CH_2)_t$—$OPO_3^{2-}$ or for the formulae A to C,

A

B

C where s stands for an integer from the range 1 to 1000, t stands for an integer selected from 1, 2, 3 or 4, and w stands for an integer selected from 1, 2 or 3.

The preferred anionic groups here include, in particular, —$COO^-$, —$SO_3^-$, —$OSO_3^-$, —$PO_3^{2-}$, —$OPO_3^{2-}$, the subformula A, and —$(OCH_2CH_2)_s$—O—$(CH_2)_t$—$COO^-$, —$(OCH_2CH_2)_s$—O—$(CH_2)_t$—$SO_3^-$ and —$(OCH_2CH_2)_s$—O—$(CH_2)_t$—$OSO_3^-$, where each individual one of these groups taken alone may be preferred.

The very particularly preferred anionic groups here include —$SO_3^-$, —$OSO_3^-$, —$PO_3^{2-}$ or $OPO_3^{2-}$, in particular —$SO_3^-$. Particular preference is given to compounds in which $Y_1$ is a sulfonate group —$SO_3^-$, and $Y_2$ is a hydrogen atom.

X is preferably a monovalent cation, in particular $H^+$, an alkali metal cation or $NR_4^+$, where $R=H^+$ or C1-C6-alkyl, and all R may be identical or different. X is particularly preferably $Na^+$, $K^+$ or $NH_4^+$, especially preferably $Na^+$.

Preferred compounds of the formula (I) are, in particular, compounds in which all variables have the preferred meanings. Preference is explicitly given to compounds in which $Z_1=Z_2=Z_3=F_3C(CF_2)_{ai}(CH_2)_{bi}(O(CH_2)_{ci})_{di}$—, where ai=1-2, bi=1-2, ci=2, di=1-3, $Y_1$ or $Y_2$ is a sulfonate group —$SO_3^-$, and $X=Na^+$.

Particular preference is given to compounds of the formula (Ia) or (Ib):

(Ia)

(Ib)

where $Z_1=Z_2=Z_3$ and all $Z_i$ are selected from $R_i(O(CH_2)_{ci})_{di}-$, where ci=2, di=1-3, and $R_i=CF_3CF_2CH_2-$ or $CF_3CF_2CF_2CH_2-$.

The compounds of the formula (I) according to the invention are referred to in the present invention as sulfotricarballylates and are based on esters of aconitic acid, onto the double bond of which a sulfonate group has been added. In particular, sulfotricarballylates containing three fluorinated end groups according to the invention are preferred. The compounds of the formula (I) according to the invention can also be in the form of mixtures, particularly also in the form of isomer mixtures (constitutional and/or configurational isomer mixtures). In particular, diastereomer and/or enantiomer mixtures are possible.

Examples of preferred compounds according to the invention are:

(Ia-1)

(Ia-2)

(Ib-2)

-continued (Ia-3)

(Ia-4)

(Ia-5)

(Ia-6)

where compounds of the formulae Ia-1 and Ia-2 are particularly preferred.

Advantages of the compounds according to the invention may be, in particular:
- a surface activity which is equal or superior to that of conventional hydrocarbon surfactants with respect to efficiency and/or effectiveness,
- biological and/or abiotic degradability of the substances without the formation of persistent perfluorinated degradation products, such as PFOA (perfluorooctanoic acid) or PFOS (perfluorooctanesulfonate),
- weak foaming action and/or low foam stabilisation,
- good processability in formulations and/or
- storage stability.

The compounds according to the invention preferably have particular surface activity. The compounds of the formula (I) according to the invention may have significantly improved environmental properties compared with the prior-art fluorosurfactants since they do not undergo either chemical or biological degradation to long-chain PFCAs or PFASs.

The present invention relates secondly to the use of the compounds according to the invention, in particular the preferred compounds of the formula (I), as surface-active agents, for example for improving the flow behaviour and wetting ability of coating formulations.

The preferred embodiments of the compounds according to the invention described above can particularly advantageously be used here. Sulfotricarballylates which contain two or three, in particular three, fluorinated groups according to the invention are preferably used. Compounds of the formulae (Ia) and/or (Ib) are preferably used. The compounds according to the invention can also be used in the form of mixtures, particularly also in the form of isomer mixtures (constitutional and/or configurational isomer mixtures). In particular, diastereomer and/or enantiomer mixtures are possible.

Areas of application are, for example, the use of the compounds according to the invention as additives in surface-coating preparations, such as paints, coatings, protective coatings, speciality coatings in electronic or semiconductor applications (for example photoresists, top antireflective coatings, bottom antireflective coatings) or in optical applications (for example photographic coatings, coatings of optical elements), in polishes and waxes (in particular for furniture, floors and automobiles), or in additive preparations for addition to corresponding preparations.

For use, the compounds according to the invention are usually incorporated into correspondingly designed preparations. The present invention likewise relates to corresponding compositions comprising at least one compound according to the invention. Such compositions preferably comprise a vehicle which is suitable for the particular application and optionally further active substances and/or optionally assistants. Preferred compositions here are paint and surface-coating preparations and printing inks.

In particular, the present invention also relates to water-based surface-coating formulations which comprise at least one of the compounds according to the invention, alone or mixed with other surfactants. Preference is given to the use of surface-coating formulations based on the following synthetic film formers:

polycondensation resins, such as alkyd resins, saturated/unsaturated polyesters,
polyamides/imides, silicone resins; phenolic resins; urea resins and melamine resins,
polyaddition resins, such as polyurethanes and epoxy resins,
polymerisation resins, such as polyolefins, polyvinyl compounds and polyacrylates.

In addition, the compounds according to the invention are also suitable for use in surface coatings based on natural products and modified natural products. Preference is given to surface coatings based on oils, polysaccharides, such as starch and cellulose, and also based on natural resins, such as cyclic oligoterpenes, polyterpenes and/or shellac. The compounds according to the invention can be used both in physically hardening (thermoplastics) and in crosslinking (elastomers and thermosets) aqueous surface-coating systems. The compounds according to the invention preferably improve the flow and wetting properties of the surface-coating systems.

A further area of application of the compounds according to the invention is in processes for the preparation of polymers, in particular fluoropolymers. Important industrial methods for the preparation of fluoropolymers, such as, for example, polytetrafluoroethylene (PTFE), are, for example, emulsion and suspension polymerisation. Suspension and emulsion polymerisation processes are standard polymerisation processes which are well known to the person skilled in the art. In suspension and emulsion polymerisation processes, the system always comprises at least four constituents: (predominantly) water-insoluble monomer, water, dispersant or emulsifier and initiator. The performance of the said polymerisation processes is familiar to the person skilled in the art. In these processes, the polymer is prepared in an autoclave which contains water, the corresponding, usually gaseous, monomer(s), initiator(s), surfactant(s) and other assistant(s), with stirring and constant temperature and pressure control. The compounds according to the invention are suitable as surfactants for keeping the very hydrophobic fluoropolymer droplets or particles dispersed in the aqueous solution.

In addition, the compounds according to the invention can be employed in hydrophobicising agents, oleophobicising agents, wetting/flow-control agents, spot and soiling protectors/cleaning agents, stain releases, antifogging agents, lubricants, antifoams, deaerators, drying accelerators, abrasion resistance and mechanical wear enhancers, and antistatics, in particular in the treatment of textiles (in particular clothing, carpets and carpeting, upholstery in furniture and automobiles) and hard surfaces (in particular kitchen surfaces, sanitaryware, tiles, glass), non-woven textile materials, leatherware, papers and cardboard, wood and wood-based materials, mineral substrates, such as stone, cement, concrete, plaster, ceramics (glazed and unglazed tiles, stoneware, porcelain) and glasses, and for plastics and metallic substrates. For metallic substrates, the claims additionally also relate to the use in anticorrosion agents. For plastics and moulds for plastics processing, the claims additionally also relate to the use in mould-release agents. In the case of cleaning agents and spot removers, the claims additionally also relate to the use as detergent or soiling emulsifier and dispersant.

The compounds according to the invention can furthermore be used as antimicrobial active substance, in particular as reagent for antimicrobial surface modification.

A further area of application of the compounds according to the invention is in additives or in additive preparations in printing inks, having one or more of the following functions: antifoam, deaerator, friction-control agent, wetting agent, flow-control agent, pigment compatibility enhancer, print resolution enhancer, drying accelerator.

The compounds according to the invention can also be used as foam stabilisers and/or for supporting film formation, in particular in aqueous film-forming fire-extinguishing foams, both synthetic and protein-based, also for alcohol-resistant formulations (AFFF and AFFF-AR, FP, FFFP and FFFP-AR).

The compounds according to the invention can furthermore be employed as additives in polymeric materials (plastics), having one or more of the following functions: lubricant, internal friction reducer, UV stabiliser, hydrophobicising agent, oleophobicising agent, spot and soiling protector, coupling agent for fillers, flameproofing agent, migration inhibitor (in particular against migration of plasticisers), antifogging agent.

In addition, the compounds according to the invention are also suitable for use as additives in liquid media for cleaning, etching, reactive modification and/or substance deposition on metal surfaces (in particular also electrocoating and anodisation) or semiconductor surfaces (in particular for semiconductor photolithography: developer, stripper, edge bead remover, etching agent and cleaning agent), as wetting agent and/or deposited film quality enhancer.

In addition, the compounds which can be used in accordance with the invention as surfactant are suitable for washing and cleaning applications, and for use as additives/surfactants in cosmetic products, such as, for example, hair and body care products (for example shampoos, hair rinses and hair conditioners), foam baths, creams or lotions, having one or more of the following functions: emulsifier, wetting agent, foaming agent, lubricant, antistatic, skin grease resistance enhancer.

The compounds according to the invention are furthermore used as additives in herbicides, pesticides and fungicides, having one or more of the following functions: substrate wetting agent, adjuvant, foam inhibitor, dispersant, emulsion stabiliser. In addition, the compounds according to the invention can also be used as additives in de-icing agents or anti-icing agents.

In addition, the compounds according to the invention are suitable as additives in preparations for ore processing, in particular flotation and leaching solutions, having one or more of the following functions: wetting agent, foaming agent, foam inhibitor, and as additives in agents for the stimulation of oil wells, having one or more of the following functions: wetting agent, foaming agent, emulsifier.

A further area of application of the compounds according to the invention is in the use as additives in adhesives, having one or more of the following functions: wetting agent, penetrant, substrate adhesion enhancer, antifoam.

The compounds according to the invention can furthermore be employed as additives in greases and hydraulic fluids, having one or more of the following functions: wetting agent, corrosion inhibitor. In the case of greases, the claims additionally also relate to the use as dispersant (in particular for fluoropolymer particles).

The compounds according to the invention can also be used as additives in putties and filling compositions, having one or more of the following functions: hydrophobicising agent, oleophobicising agent, soiling protector, weathering resistance enhancer, UV stabiliser, agent against silicone bleeding.

The present invention relates to all uses mentioned here of compounds to be employed in accordance with the invention. The respective use of surfactants for the said purposes is known to the person skilled in the art, and consequently use of the compounds to be employed in accordance with the invention will present no problems. The compounds of the formula (I) according to the invention are preferably used in paint and coating preparations, printing inks and waxes, as well as polishes. Particular preference is given to the use in paint and coating preparations.

The use of compounds of the formula (I), in particular the compounds of the formula (I) described as preferred above, in paint and coating preparations is particularly advantageous. Compounds in which the groups $Z_i$ are equal to $R_i(O(CH_2)_{ci})_{di}$—, where the respective indices ci=2-10, preferably 2-4, in particular 2, and di=0-5, preferably 1-3, in particular 1, are preferred here. Compounds of the formula (I) in which $Z_1=Z_2=Z_3=F_3C(CF_2)_{ai}$—$(CH_2)_{bi}(O(CH_2)_{ci})_{di}$—, where ai=0-6, preferably 1-5, in particular 1-2, bi=1-6, preferably 1-3, in particular 1-2, ci=2, di=1-3, preferably 1, $Y_1$ or $Y_2$ is equal to a sulfonate group —$SO_3^-$, and X=$Na^+$, are particularly preferred. In particular, compounds of the formulae Ia-1 to Ia-6 are suitable for use in paint and coating preparations, particularly those of the formulae Ia-1 and Ia-2.

The compounds of the formula (I) according to the invention can preferably be prepared by esterification of aconitic acid or the anhydride or acid chloride or of citric acid using one or more alcohols $Z_iOH$ (II) followed by an addition reaction, preferably of sodium hydrogensulfite.

$Z_i$ is an unfluorinated, branched or unbranched, alkyl group or a group of the structure $R_i(A(CR^1R^2)_{ci}(CR^3R^4)_{c'i})_{di}$—, where the respective indices ci and c'i are, independently of one another, 0-10, and di=0-5, where $R_i$ is a branched or unbranched, fluorine-containing alkyl radical, $R^1$ to $R^4$ are, independently of one another, hydrogen or a branched or unbranched alkyl group, ci and c'i are not simultaneously 0, and A=O, S and/or N. $Z_i$ preferably encompasses the variables described for the preferred compounds of the formula (I), in particular an $F_3C(CF_2)_{ai}(CH_2)_{bi}(O(CH_2)_{ci})_{di}$— group, where ai=0-6, bi=1-6, ci=2-10, and di=0-5. ai is preferably equal to 1 or 2, bi is preferably equal to 1 to 3, in particular 1 to 2. ci is preferably equal to 2 to 4, in particular 2. di is preferably equal to 1 to 3, in particular 1.

Preference is given to the use of alcohols containing $F_3C(CF_2)_{ai}(CH_2)_{bi}$—$(O(CH_2)_{ci})_{di}$— groups, where one or also various alcohols can be reacted as a mixture or in steps. Preferably, only one alcohol is used, in particular.

The esterification can also be carried out in a mixture with unfluorinated, branched or unbranched alcohols or in steps using various alcohols. The unfluorinated, branched or unbranched alcohols are preferably those containing linear or branched alkyl having 1 to 20 C atoms, preferably 1 to 10 C atoms. Particular preference is given to alcohols having 3 to 10 C atoms, particularly preferably having 3 to 8 C atoms.

The present invention thus relates thirdly to a process for the preparation of compounds of the formula (I), in particular sulfotricarballylates, which contain two or three end groups which are fluorinated in accordance with the invention.

The alcohols used are commercially available and/or their preparation is familiar to the person skilled in the art (Heilmann et al. J. Fluorine Chem. 1992, 59, 387; Janulis et al. U.S. Pat. No. 5,157,159 (1992)).

The aconitic esters are preferably synthesised in the presence of a conventional catalyst, such as, for example, toluene-4-sulfonic acid monohydrate:

The aconitic esters can furthermore preferably be synthesised starting from citric acid in the presence of a conventional catalyst, such as, for example, sulfuric acid. It is also possible to prepare the corresponding citric acid esters (IV).

In a second step, the group Y is then introduced by an addition reaction onto the double bond of the aconitic esters or derivatisation of the OH group of the citric acid esters by methods familiar to the person skilled in the art. The following scheme shows by way of example the synthesis of the sulfotricarballylates by the addition reaction of sodium hydrogensulfite, which can be carried out under conditions known to the person skilled in the art:

The formula (III) reproduces the presence of Z/E double-bond isomers. Further compounds according to the invention can be prepared analogously to the illustrative reactions shown above. Further compounds according to the invention can also be prepared by other methods known from the literature and known per se to the person skilled in the art. In particular, other esterification catalysts can be used.

The present invention relates fourthly to compounds of the formula (III), which occur as intermediates in the above-described syntheses of the compounds of the formula (I) according to the invention:

where the groups $Z_i$ ($Z_1$, $Z_2$ and $Z_3$) are, independently of one another, branched or unbranched alkyl groups or groups of the structure $R_i(A(CR^1R^2)_{ci}-(CR^3R^4)_{c'i})_{di}-$, where the respective indices ci and c'i are, independently of one another, 0-10, preferably 0-6, in particular 0-2, and di=0-5, where $R_i$ is a branched or unbranched, fluorine-containing alkyl radical, $R^1$ to $R^4$ are, independently of one another, hydrogen or a branched or unbranched alkyl group, ci and c'i are preferably not simultaneously 0, A=O, S and/or N, and at least one of the groups $Z_i$ is a group of the structure $R_i(A(CR^1R^2)_{ci}(CR^3R^4)_{c'i})_{di}-$.

Preferred compounds of the formula (III) are those in which $Z_1$, $Z_2$ and $Z_3$ are, independently of one another, $F_3C(CF_2)_{ai}(CH_2)_{bi}(O(CH_2)_{ci})_{di}-$ groups, where ai=0-6, in particular ai=1-5, preferably 1-2, bi=1-6, preferably 1-3, in particular bi=1-2, ci=2-10, in particular ci=2, and di=0-5, in particular di=1. Particularly suitable compounds are those where $Z_1=Z_2=Z_3$.

Preference is also given to compounds in which ai=0, 1 or 2, preferably 1 or 2, in particular 1, bi=1, ci=2, and di=1 or 2, in particular 1, and where $a_1+a_2+a_3>1$.

The present invention relates fifthly to the use of the compounds of the formula (III) as monomers or comonomers in the synthesis of fluorinated polymers.

The disclosures in the cited references are hereby expressly also part of the disclosure content of the present application. The following examples explain the present invention in greater detail without restricting the scope of protection.

EXAMPLES

Example 1

Synthesis of the sulfotricarballylate of the Formula (Ia-1)

a) Esterification

The alcohol used is prepared as described in the literature (Heilmann et al. J. Fluorine Chem. 1992, 59, 387; Janulis et al. U.S. Pat. No. 5,157,159 (1992)). A mixture of 72.4 mmol of alcohol, 18.1 mmol of aconitic acid (90%, Alfa Aesar) and 3.6 mmol of toluene-4-sulfonic acid monohydrate (Merck KGaA) in 40 ml of toluene is subsequently stirred under reflux for 48 hours. The water liberated during the reaction is removed with the aid of a water separator. The reaction is quenched using water. The mixture is subsequently extracted with toluene, and the combined organic phases are washed with water, dried over sodium sulfate and filtered. The solvent is distilled off in a rotary evaporator.

Purification: column chromatography over silica gel; Eluent: toluene/ethyl acetate 1/2
Substance: $C_{21}H_{21}F_{15}O_9$, M=702.362 g/mol
$^1$H-NMR (400 MHz; in DMSO-$d_6$):
6.84 (s); 4.38-4.09 (m); 3.92-3.74 (m) ppm.
$^{19}$F-NMR (376 MHz; in DMSO-$d_6$):
−82.85−−83.02 (m); −122.79−−122.94 (m) ppm.
MS (EI, 70 eV) m/e:
553 (10%); 509 (10%); 221 (15%); 177 (100%).

b) Addition Reaction

-continued 68 ml of sodium hydrogensulfite solution (39% in water, Merck KGaA) (338 mmol) are added dropwise at 50° C. to a solution of 13.5 mmol of the triester in 45 ml of 1,4-dioxane (Merck KGaA), and the mixture is stirred under reflux. After the dropwise addition, the reaction temperature is held at 88° C. for 65 hours. After 24 hours and 48 hours, 23 ml of sodium hydrogensulfite solution (39% in water, Merck KGaA) (113 mmol) are again added dropwise each time. The solvent is removed in a rotary evaporator. The crude product is subsequently taken up in diethyl ether (Merck KGaA), stirred and filtered. The filter residue is again washed by stirring and filtered. The diethyl ether phases are combined, and the organic solvent is removed in a rotary evaporator.

Substance: $C_{21}H_{22}F_{15}O_{12}SNa$; M=806.424 g/mol $^1$H-NMR (400 MHz; in DMSO-$d_6$):
4.31-4.06 (m); 4.00 (d); 3.95 (d); 3.88-3.71 (m); 3.68-3.54 (m); 3.48-3.37 (m); 3.36-3.00 (m); 2.92 (d); 2.87 (d) ppm.

$^{19}$F-NMR (376 MHz; in DMSO-$d_6$):
−83.23−−83.40 (m); −123.16−−123.55 (m) ppm.

MS (FIA-ESI) m/e:
Pos. mode: 807 (M+H)$^+$
Neg. mode: 783 (M−Na)$^-$

Example 2

Determination of the Static Surface Tension

The static surface tensions γ of aqueous surfactant solutions having various concentrations c (percent by weight) are determined.

Instrument: Sinterface tensiometer (model PAT1)
Temperature of the measurement solutions: room temperature Measurement method employed: measurement of the surface tension on hanging droplets against air. The principal radii of curvature ($r_1$ and $r_2$) of the ellipsoids (droplets) are determined here by droplet contour analysis. Since the pressure difference (Δp) between the outside and inside of an interface is indirectly proportional to the radii of curvature, the surface tension can be calculated from the following correlation:

$$\Delta p = \gamma \left( \frac{1}{r_1} + \frac{1}{r_2} \right)$$

Instrument settings: droplet volumes 7-10 mm$^3$; measurement time 1500-3600 s; 1.5 pictures/s, droplet density=1 g/cm$^3$.

The measurement values are shown in Table 1. FIG. 1 shows the static surface tension as a function of the concentration of the sulfocarballylate according to Example 1b).

TABLE 1

| c [%] | γ[mN/m] |
| --- | --- |
| 0.001 | 49.4 |
| 0.013 | 35.6 |
| 0.127 | 28.5 |
| 0.240 | 24.7 |
| 0.308 | 22.9 |
| 0.370 | 22.6 |
| 0.414 | 22.3 |
| 0.451 | 21.9 |
| 0.485 | 21.2 |
| 0.513 | 20.9 |
| 0.610 | 21.2 |
| 1.265 | 20.7 |

Example 3

Determination of the Dynamic Surface Tension

The dynamic surface tension γ of a 0.1% (percent by weight) aqueous solution of compound 1b) is determined.

Measurement method employed: measurement of the surface tension using the bubble pressure method Instrument: SITA tensiometer (model t 60)
Temperature of the measurement solutions: 21° C.±0.2° C.

In the measurement of the dynamic surface tension, air bubbles are forced through a capillary into the surfactant solution at different rates. From the resultant pressure change, the surface tension can be determined as a function of the bubble life using the following equation:

$$\gamma = \frac{r(p_{max} - \rho \cdot g \cdot h)}{2}$$

$p_{max}$=maximum pressure, ρ=density of the liquid, h=immersion depth, r=radius of the capillary The measurement values are shown in Table 2. FIG. 2 shows the dynamic surface tension as a function of the bubble life for compound 1b).

TABLE 2

| Bubble life [ms] | γ[mN/m] |
|---|---|
| 30 | 56.1 |
| 38 | 51.5 |
| 50 | 47.7 |
| 65 | 44.1 |
| 82 | 41.9 |
| 113 | 40 |
| 141 | 38.8 |
| 189 | 37.9 |
| 243 | 37.2 |
| 306 | 36.3 |
| 414 | 35.7 |
| 533 | 35.6 |
| 674 | 35.2 |
| 924 | 34.6 |
| 1299 | 34.2 |
| 1727 | 33.9 |
| 2200 | 33.7 |
| 2507 | 33.5 |
| 3204 | 33.5 |
| 4102 | 32.9 |
| 5473 | 32.9 |
| 7012 | 32.7 |
| 9132 | 32.5 |
| 11537 | 32.3 |
| 15707 | 32.1 |
| 19795 | 31.8 |
| 26529 | 31.5 |
| 35138 | 31.4 |
| 44790 | 31.3 |
| 58574 | 31 |

Example 4

Antipitting Test in a Polyurethane Water-Borne Surface Coating

A surface coating is prepared from the raw materials according to Table 3 in which surface defects (pits) are generated specifically by overdosing the antifoam BYK 023. A highly concentrated solution (95% by weight) of the sulfotricarballylate according to Example 1b in Dowanol PM (Dow Chemicals) is incorporated into the surface coating in various amounts and compared in efficacy to the 0 sample (without sulfotricarballylate).

TABLE 3

Raw materials for surface-coating formulation

| Product | Function | Manufacturer |
|---|---|---|
| Bayhydrol XP 2470 | Binder | Bayer |
| Bayhydur 304 | PUR curing agent | Bayer |
| Methoxybutyl acetate | Solvent | VWR |
| BYK-023 | Antifoam | BYK Chemie |
| Blue pigment paste | Contrast to substrate | BASF |

In the preparation of the contaminated surface-coating sample, firstly binder, pigment paste and water are initially introduced (Table 4a; PE beaker: 860 ml), and some of the initially introduced mixture is subsequently completed (Table 4b; PE beaker 350 ml).

TABLE 4a

Initially introduced components 1

| Pos. | Raw material | Formulation [g] | Dissolver/stirrer disc setting |
|---|---|---|---|
| 1 | Bayhydrol XP 2470 | 271.18 | 400 rpm; 10 min; 80 mm |
| 2 | Pigment paste | 8 | |
| 3 | H$_2$O | 27.28 | |

TABLE 4b

Completion

| Pos. | Raw material | Formulation [g] | Dissolver/stirrer disc setting |
|---|---|---|---|
| 4 | Initially introduced mixture | 128.55 | 400 rpm; 10 min; 80 mm |
| 5 | Bayhydur 304 | 41.03 | |
| 6 | Methoxybutyl acetate | 10.27 | |
| 7 | H$_2$O | 19.62 | |
| 8 | BYK 023 | 0.14 | 600 rpm; 10 min; 60 mm |

For incorporation of the surfactant solution, the latter is firstly initially introduced (PE beaker, 175 ml), and the amount of surface coating is subsequently based on the weight of surfactant. Three test coatings having a different surfactant content or without surfactant are prepared (Table 5).

TABLE 5

Incorporation of the surfactant solution

| Surface-coating sample | Weight of surfactant solution [g] | Weight of surface coating [g] | C* surfactant [%] | Dissolver/stirrer disc setting |
|---|---|---|---|---|
| 1 | — | — | 0 sample | — |
| 2 | 0.0544 | 37.42 | 0.06 | 900 rpm; 5 min; 40 mm |
| 3 | 0.2064 | 47.39 | 0.19 | 900 rpm; 5 min; 40 mm |

*Surfactant content based on the total amount of surface-coating sample

The surface coatings are applied to white paint cards (219× 286 mm; manufacturer: Leneta) with the aid of an automatic film applicator with vacuum suction (Byk Gardner E-2101) with a film applicator frame (Erichson model 360; capacity: 4 ml of surface coating; metering: 20 ml spraying; drawing speed: 50 mm/s; wet layer thickness: 30 μm).

Surface-coating sample 2 is virtually free of surface defects (pits) and surface-coating sample 3 is completely free of surface defects (pits), whereas surface-coating sample 1 exhibits numerous surface defects (pits).

FIGS. 1 and 2 show the static and dynamic surface tension respectively for compound 1b).

Example 5

Synthesis of the sulfotricarballylate of the Formula (Ia-2)

The sulfotricarballylate of the formula (Ia-2) is prepared by the process described in Example 1.

Empirical formula: $C_{24}H_{22}F_{21}O_{12}SNa$, M=956.447 g/mol $^1$H-NMR (300 MHz; in DMSO-d$_6$):
4.26-4.02 (m); 3.91 (dd); 3.82-3.67 (m); 3.63-3.46 (m); 3.44-3.30 (m); 3.25-2.98 (m);
2.89-2.77 (m) ppm.
$^{19}$F-NMR (282 MHz; in DMSO-d$_6$):
−80.42 to −80.82 (m); −127.11 to −127.50 (m); −119.79 to −120.88 (m) ppm.
MS (FIA-ESI) m/e:
Neg. mode: 933 (M−Na)$^-$ Both the static surface tension as described in Example 2 and the dynamic surface tension as described in Example 3 are subsequently determined. The results are shown in Tables 6 and 7.

TABLE 6

| c [%] | γ [mN/m] |
|---|---|
| 0.0001 | 54.2 |
| 0.0011 | 30.6 |
| 0.0018 | 27.8 |
| 0.0055 | 25.8 |
| 0.011 | 21.5 |
| 0.016 | 18.4 |
| 0.038 | 17.8 |
| 0.045 | 17.8 |
| 0.050 | 17.8 |
| 0.024 | 17.8 |
| 0.100 | 17.6 |
| 0.994 | 17.6 |

TABLE 7

| Bubble life [ms] | γ [mN/m] |
|---|---|
| 31 | 68 |
| 38 | 66.3 |
| 49 | 62.7 |
| 65 | 58.4 |
| 83 | 52.1 |
| 108 | 44.7 |
| 144 | 34.8 |
| 191 | 27.7 |
| 241 | 25 |
| 325 | 22.9 |
| 406 | 20.4 |
| 522 | 19.3 |
| 697 | 18.9 |
| 859 | 18.8 |
| 1163 | 18.3 |
| 1811 | 18.1 |
| 2250 | 17.8 |
| 2590 | 17.8 |
| 3223 | 17.6 |
| 4028 | 17.4 |
| 5615 | 17.6 |
| 7247 | 17.5 |
| 8998 | 17.4 |
| 12741 | 17.2 |
| 16566 | 17.5 |
| 19736 | 17.1 |
| 27035 | 17.3 |
| 34338 | 16.9 |
| 43556 | 16.8 |
| 56679 | 16.8 |

Example 6

Synthesis of the sulfotricarballylate of the Formula (Ia-3)

The sulfotricarballylate of the formula (Ia-3) is prepared by the process described in Example 1.

Empirical formula: C$_{21}$H$_{19}$F$_{18}$O$_{12}$SNa, M=860.395 g/mol
$^1$H-NMR (400 MHz; in DMSO-d$_6$):
5.48-5.37 (m); 5.35-5.21 (m); 4.30-4.09 (m); 4.07-3.90 (m); 3.57-3.46 (m); 3.40-3.32 (m); 3.15-3.05 (m); 2.82 (dd) ppm.
$^{19}$F-NMR (376 MHz; in DMSO-d$_6$):
−73.53 to −73.85 (m) ppm.
MS (LC-ESI-MS negative):
RT: 9.05 (837 [M−H]$^-$)

Both the static surface tension as described in Example 2 and the dynamic surface tension as described in Example 3 are subsequently determined. The results are shown in Tables 8 and 9.

TABLE 8

| c [%] | γ [mN/m] |
|---|---|
| 0.0001 | 57.9 |
| 0.001 | 52.5 |
| 0.01 | 44.0 |
| 0.10 | 29.2 |
| 0.25 | 25.4 |
| 0.53 | 22.7 |
| 1.03 | 21.7 |
| 1.22 | 21.3 |
| 2.46 | 21.0 |
| 4.74 | 20.8 |

TABLE 9

| Bubble life [ms] | γ [mN/m] |
|---|---|
| 57 | 31 |
| 53.1 | 38 |
| 47.8 | 52 |
| 44.7 | 64 |
| 42 | 85 |
| 39.8 | 111 |
| 38.7 | 144 |
| 37.4 | 190 |
| 36.5 | 243 |
| 36 | 324 |
| 35.5 | 423 |
| 35.2 | 512 |
| 34.9 | 706 |
| 34.6 | 938 |
| 34.4 | 1209 |
| 34 | 1773 |
| 33.8 | 2145 |
| 33.7 | 2498 |
| 33.6 | 3277 |
| 33.5 | 4172 |
| 33.2 | 5331 |
| 33.1 | 7431 |
| 33.1 | 9743 |
| 33.4 | 11981 |
| 32.7 | 15946 |
| 32.2 | 20560 |
| 32.1 | 27476 |
| 32.1 | 35812 |
| 32 | 47092 |
| 31.9 | 60416 |

Example 7

Synthesis of the sulfotricarballylate of the Formula (Ia-4)

The sulfotricarballylate of the formula (Ia-4) is prepared by the process described in Example 1.
Empirical formula: C$_{24}$H$_{16}$F$_{27}$O$_9$SNa, M=1016.391 g/mol $^1$H-NMR (400 MHz; in DMSO-$d_6$):
4.51-4.25 (m); 4.14 (d); 4.08 (d); 3.70-3.59 (m); 3.55-3.45 (m); 3.37-3.15 (m); 2.97 (dd) ppm.

$^{19}$F-NMR (376 MHz; in DMSO-$d_6$):
−80.95 to −81.39 (m); −113.39 to −114.00 (m); −124.36 to −124.82 (m);
−126.02 to −126.38 (m) ppm.

MS (LC-ESI-MS negative):
RT: 10.60 (993 [M−H]$^-$)

Both the static surface tension as described in Example 2 and the dynamic surface tension as described in Example 3 are subsequently determined. The results are shown in Tables 10 and 11.

TABLE 10

| c [%] | γ[mN/m] |
|---|---|
| 0.0001 | 71.6 |
| 0.0003 | 66.3 |
| 0.0006 | 40.8 |
| 0.0010 | 22.4 |
| 0.0018 | 17.6 |
| 0.0020 | 17.5 |
| 0.0024 | 17.0 |
| 0.005 | 16.8 |
| 0.01 | 16.6 |
| 0.10 | 16.3 |
| 0.93 | 16.2 |

TABLE 11

| Bubble life [ms] | γ[mN/m] |
|---|---|
| 31 | 72.3 |
| 38 | 72.2 |
| 49 | 72.1 |
| 68 | 72.1 |
| 84 | 72.2 |
| 112 | 71.8 |
| 145 | 71.9 |
| 190 | 71.6 |
| 244 | 71.3 |
| 320 | 71.3 |
| 391 | 71 |
| 521 | 71 |
| 706 | 70.5 |
| 869 | 70.2 |
| 1224 | 70.4 |
| 1613 | 70 |
| 2102 | 70.3 |
| 2572 | 70.2 |
| 3329 | 69.5 |
| 4290 | 69.2 |
| 5506 | 68.5 |
| 6850 | 67.5 |
| 9319 | 65.7 |
| 11716 | 64.2 |
| 15108 | 60 |
| 19279 | 55.8 |
| 24035 | 50.2 |
| 30865 | 40.8 |
| 40016 | 32.1 |
| 55320 | 24.4 |

Example 8

Synthesis of the sulfotricarballylate of the Formula (Ia-5)

The sulfotricarballylate of the formula (Ia-5) is prepared by the process described in Example 1.

Empirical formula: $C_{30}H_{16}F_{39}O_9SNa$, M=1316.436 g/mol $^1$H-NMR (300 MHz; in DMSO-$d_6$):
4.53-4.25 (m); 4.13 (d); 4.06 (d); 3.69-3.60 (m); 3.54-3.46 (m); 3.27 (ddd); 3.04-2.96 (m); 2.61-2.42 (m) ppm.

$^{19}$F-NMR (282 MHz; in DMSO-$d_6$):
−81.74 to −82.27 (m); −113.61 to −114.41 (m); −122.50 (s); −123.29 to −124.35 (m);
−126.74 to −127.31 (m) ppm.

MS (LC-ESI-MS negative):
RT: 11.91 (1293 [M−H]$^-$)

Both the static surface tension as described in Example 2 and the dynamic surface tension as described in Example 3 are subsequently determined. The results are shown in Tables 12 and 13.

TABLE 12

| c [%] | γ[mN/m] |
|---|---|
| 0.0001 | 71.9 |
| 0.001 | 71.5 |
| 0.01 | 71.4 |
| 0.10 | 52.9 |
| 0.98 | 54.5 |

TABLE 13

| Bubble life [ms] | γ[mN/m] |
|---|---|
| 31 | 72.8 |
| 38 | 72.9 |
| 49 | 72.8 |
| 64 | 72.8 |
| 86 | 72.9 |
| 110 | 72.7 |
| 146 | 72.7 |
| 187 | 72.9 |
| 244 | 72.9 |
| 319 | 73.1 |
| 393 | 73.2 |
| 524 | 73.3 |
| 715 | 73.4 |
| 890 | 73.3 |
| 1257 | 73.1 |
| 1614 | 72.9 |
| 2142 | 73 |
| 2536 | 73 |
| 3283 | 72.8 |
| 4222 | 72.8 |
| 5476 | 72.8 |
| 7128 | 72.9 |
| 9188 | 72.7 |
| 11868 | 72.7 |
| 15248 | 72.5 |
| 20919 | 72.5 |
| 26720 | 72.3 |
| 34303 | 72.3 |
| 44207 | 72.1 |
| 60491 | 72.2 |

Example 9

Synthesis of the sulfotricarballylate of the Formula (Ia-6)

The sulfotricarballylate of the formula (Ia-6) is prepared by the process described in Example 1.

Empirical formula: $C_{30}H_{22}F_{33}O_{12}SNa$, M=1256.492 g/mol $^1$H-NMR (400 MHz; in DMSO-$d_6$):
4.28-4.05 (m); 3.91 (d); 3.84 (d); 3.82-3.69 (m); 3.51-3.45 (m); 3.39-3.30 (m); 3.25-3.09 (m); 3.02 (dd); 2.83 (dd) ppm.

$^{19}$F-NMR (376 MHz; in DMSO-$d_6$):
−80.94 to −81.23 (m); −119.39 to −119.96 (m); −123.34 to −123.87 (m); −126.30 to −126.76 (m) ppm.
MS (LC-ESI-MS negative):
RT: 11.38 (1233 [M−H]$^-$)

Both the static surface tension as described in Example 2 and the dynamic surface tension as described in Example 3 are subsequently determined. The results are shown in Tables 14 and 15.

TABLE 14

| c [%]  | γ [mN/m] |
|--------|----------|
| 0.0001 | 72.2     |
| 0.0011 | 72.1     |
| 0.0020 | 65.0     |
| 0.0023 | 60.6     |
| 0.0033 | 44.0     |
| 0.0038 | 26.8     |
| 0.0050 | 15.8     |
| 0.0100 | 15.7     |
| 0.10   | 15.4     |
| 1.00   | 15.4     |

TABLE 15

| Bubble life [ms] | γ [mN/m] |
|------------------|----------|
| 31    | 71.7 |
| 40    | 71.4 |
| 51    | 71.4 |
| 64    | 70.9 |
| 84    | 70.9 |
| 111   | 70.9 |
| 144   | 70.4 |
| 186   | 70.4 |
| 244   | 70.1 |
| 322   | 69.8 |
| 398   | 69.7 |
| 525   | 69.6 |
| 715   | 69.5 |
| 934   | 68.7 |
| 1221  | 67.7 |
| 1597  | 67.2 |
| 2099  | 66   |
| 2501  | 65.3 |
| 3243  | 64.3 |
| 4142  | 62.3 |
| 5208  | 61   |
| 7135  | 58.1 |
| 8938  | 55.7 |
| 11481 | 53.5 |
| 15165 | 50.3 |
| 19619 | 48.2 |
| 24941 | 46.1 |
| 33879 | 44   |
| 41071 | 41.8 |
| 54632 | 40.7 |

The invention claimed is:

1. A compound of the formula (I)

$$Z_1-O-C(=O)-CH_2-C(C(=O)-O-Z_2)(Y_2)-CH(Y_1)-C(=O)-O-Z_3 \quad X \qquad (I)$$

where either:
(A) the groups $Z_i$ ($Z_1$, $Z_2$ and $Z_3$) are, independently of one another, branched or unbranched alkyl groups or groups of the structure $R_f(A(CR^1R^2)_{ci}(CR^3R^4)_{c'i})_{di}$—, where the respective indices ci and c'i are, independently of one another, 0-10 and di=1-5, where $R_f$ is a branched or unbranched, fluorine-containing alkyl radical, $R^1$ to $R^4$ are, independently of one another, hydrogen or a branched or unbranched alkyl group, ci and c'i are not simultaneously 0, and A=O, S and/or N, $Y_1$ is an anionic polar group and $Y_2$ is a hydrogen atom, or $Y_1$ is a hydrogen atom and $Y_2$ is an anionic polar group, X is a cation, and at least one of the groups $Z_i$ is a group of the structure $R_f(A(CR^1R^2)_{ci}-(CR^3R^4)_{c'i})_{di}$—; or (B) the groups $Z_i$ ($Z_1$, $Z_2$ and $Z_3$) are, independently of one another, branched or unbranched alkyl groups or groups of the structure $R_f(A(CR^1R^2)_{ci}(CR^3R^4)_{c'i})_{di}$—, where the respective indices ci and c'i are, independently of one another, 0-10 and di=0-5, where $R_f$ is a branched or unbranched, fluorine-containing alkyl radical, $R^1$ to $R^4$ are, independently of one another, hydrogen or a branched or unbranched alkyl group, ci and c'i are not simultaneously 0, and A=O, S and/or N, $Y_1$ is an anionic polar group and $Y_2$ is a hydrogen atom, provided that, when $Y_1$ is the anionic polar group sulfonate, —SO$_3^-$, $Z_1$, $Z_2$ and $Z_3$ are not simultaneously —CH$_2$(CF$_2$)$_3$CF$_2$H, —CH$_2$(CF$_2$)$_2$CF$_3$, or —CH$_2$CF$_2$CHFCF$_3$, X is a cation and at least one of the groups $Z_i$ is a group of the structure $R_f(A(CR^1R^2)_{ci}-(CR^3R^4)_{c'i})_{di}$—.

2. A compound according to claim 1, wherein the variables in the formula (I) have the following meanings:
the groups $Z_i$ ($Z_1$, $Z_2$ and $Z_3$) are, independently of one another, branched or unbranched alkyl groups or groups of the structure $R_f(O(CH_2)_{ci})_{di}$, where the respective indices ci=2-10 and di=0-5, and where $R_f$ is a branched or unbranched, fluorine-containing alkyl radical, $Y_1$ is an anionic polar group and $Y_2$ is a hydrogen atom, or vice versa $Y_1$ is a hydrogen atom and $Y_2$ is an anionic polar group, X is a cation, and at least one of the groups $Z_i$ is a group of the structure $R_f(O(CH_2)_{ci})_{di}$.

3. A compound according to claim 1, wherein the branched or unbranched alkyl groups for $Z_i$ contain 1 to 10 carbon atoms.

4. A compound according to claim 1, wherein X is a monovalent cation or an alkali metal cation.

5. A compound according to claim 1, wherein the compound has two or three fluorinated groups $Z_i$.

6. A compound according to claim 1, wherein $Z_1$, $Z_2$ and $Z_3$ are, independently of one another, $F_3C(CF_2)_{ai}(CH_2)_{bi}(O(CH_2)_{ci})_{di}$— groups, where ai=0-2, bi=1-6, ci=2-10, and di=0-5.

7. A compound according to claim 1, wherein $Y_1$ or $Y_2$ is a sulfonate group —SO$_3^-$.

8. A compound according to claim 1, wherein $Z_1=Z_2=Z_3=F_3C(CF_2)_{ai}(CH_2)_{bi}(O(CH_2)_{ci})_{di}$, where ai=1-2, bi=1-2, ci=2, and di=1, $Y_1$ is a sulfonate group —SO$_3^-$, $Y_2$ is a hydrogen atom, and X=Na$^+$.

9. A compound of the formula (Ia) or (Ib):

(Ia)

(Ib)

where $Z_1=Z_2=Z_3$ and all $Z_i$ are selected from $R_f(O(CH_2)_{c'i})_{di}$—, where ci=2, di=1-3, and $R_f$=CF$_3$CF$_2$CH$_2$— or CF$_3$CF$_2$CF$_2$CH$_2$—.

10. A composition comprising a compound according to claim 1 as a surface-active agent, in a paint or coating composition, a printing ink, a wax or a polish.

11. A paint or coating composition comprising at least one compound according to claim 1 and a vehicle which is suitable for a paint or coating composition, and optionally further active substances.

12. A process for the preparation of a compound according to claim 1, comprising a) an esterification of aconitic acid or citric acid or the anhydride or acid chloride thereof using one or more alcohols of the formula $Z_iOH$ (II), and b) an addition reaction, onto the olefinic double bond or derivitization of the OH group, where the alcohols contain groups $Z_i$ according to claim 1.

13. A compound of the formula (III)

(III)

where
the groups $Z_i$ ($Z_1$, $Z_2$ and $Z_3$) are, independently of one another, branched or unbranched alkyl groups or groups of the structure $R_i(A(CR^1R^2)_{ci}(CR^3R^4)_{c'i})_{di}$—, where the respective indices ci and c'i are, independently of one another, 0-10 and di=0-5, where $R_i$ is a branched or unbranched, fluorine-containing alkyl radical, $R^1$ to $R^4$ are, independently of one another, hydrogen or a branched or unbranched alkyl group, and A=O, S and/or N, and at least one of the groups $Z_i$ is a group of the structure $R_i(A(CR^1R^2)_{ci}(CR^3R^4)_{c'i})_{di}$—, where ci and c'i are not simultaneously 0.

14. A compound according to claim 13, wherein $Z_1$, $Z_2$ and $Z_3$ are, independently of one another, $F_3C(CF_2)_{ai}(CH_2)_{bi}(O(CH_2)_{ci})_{di}$— groups, where ai=0-6, bi=1-6, ci=2-10, and di=0-5.

15. A method for the synthesis of fluorinated polymers which comprises polymerizing a compound of the formula (III) of claim 13 as a monomer or comonomer.

16. A compound according to claim 1, wherein the branched or unbranched alkyl groups for $Z_i$ contain 3 to 8 carbon atoms.

17. A compound according to claim 1, wherein X is the monovalent cation H$^+$ or the alkali metal cation Na$^+$ or NR$_4^+$, where R=H or $C_1$-$C_6$-alkyl, and each R may be identical or different.

18. A compound according to claim 1, wherein the compound has three fluorinated groups $Z_i$.

19. A compound according to claim 1, wherein $Z_1$, $Z_2$ and $Z_3$ are, independently of one another, $F_3C(CF_2)_{ai}(CH_2)_{bi}(O(CH_2)_{ci})_{di}$— groups, where ai=1-2, bi=1-2, ci=2, and di=1.

20. A compound according to claim 6, wherein $Z_1$, $Z_2$ and $Z_3$ are the same groups.

21. A compound according to claim 1, wherein $Y_1$ is a sulfonate group, —$SO_3^-$.

22. The process of claim 12, wherein the esterification (a) is conducted in the presence of a catalyst and the addition reaction b) is by addition of sodium hydrogensulfite onto the olefinic double bond.

23. A compound according to claim 13, wherein $Z_1$, $Z_2$ and $Z_3$ are, independently of one another, $F_3C(CF_2)_{ai}(CH_2)_{bi}(O(CH_2)_{ci})_{di}$— groups, where ai=1-2, bi=1-2, ci=2, and di=1-3.

24. A compound according to claim 14, wherein $Z_1$, $Z_2$ and $Z_3$ are the same $F_3C(CF_2)_{ai}(CH_2)_{bi}(O(CH_2)_{ci})_{di}$— group.

25. A compound according to claim 1, wherein
$R^1$ to $R^4$ are, independently of one another, hydrogen or a $C_{1-4}$-alkyl group,
ci and c'i are, independently of one another, 0-6, where ci and c'i are not simultaneously 0, and
di is 1-3.

26. A compound according to claim 1, which is a compound of formula (Ia-4) or formula (ia-5)

(Ia-4)

-continued (Ia-5)

* * * * *